US007528117B2

(12) United States Patent
Wang et al.

(10) Patent No.: US 7,528,117 B2
(45) Date of Patent: May 5, 2009

(54) HIGH EFFICACY ANTISENSE RI$_\alpha$PKA POLY-DNP OLIGORIBONUCLEOTIDES

(75) Inventors: Jui H. Wang, Williamsville, NY (US); Long Shen, Tonawanda, NY (US); Xiaolan Chen, North Tonawanda, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 847 days.

(21) Appl. No.: 10/728,491

(22) Filed: Dec. 5, 2003

(65) Prior Publication Data

US 2004/0142896 A1 Jul. 22, 2004

Related U.S. Application Data

(60) Provisional application No. 60/431,594, filed on Dec. 5, 2002.

(51) Int. Cl.
*A01N 43/04* (2006.01)
*C12Q 1/68* (2006.01)
*C12P 19/34* (2006.01)
*C07H 21/02* (2006.01)
*C07H 21/04* (2006.01)

(52) U.S. Cl. ............................ 514/44; 435/6; 435/91.1; 435/91.31; 435/455; 536/23.1; 536/24.31; 536/24.5

(58) Field of Classification Search .................. 435/6, 435/91.1, 91.31, 455, 375; 536/23.1, 24.5, 536/24.31; 514/1, 2, 44
See application file for complete search history.

(56) References Cited

U.S. PATENT DOCUMENTS

| 5,271,941 A | * | 12/1993 | Cho-Chung | 424/450 |
| 5,496,546 A | | 3/1996 | Wang et al. | |
| 5,858,988 A | * | 1/1999 | Wang | 514/44 |
| 6,133,246 A | * | 10/2000 | McKay et al. | 514/44 |
| 6,291,438 B1 | | 9/2001 | Wang | |

FOREIGN PATENT DOCUMENTS

| WO | WO 96/16976 | * | 6/1996 |
| WO | WO 97/11171 | * | 3/1997 |
| WO | WO 99/50409 | * | 4/1999 |
| WO | WO 99/50409 | * | 10/1999 |

OTHER PUBLICATIONS

Agrawal, S. et al., Molecular Med. Today, vol. 6, pp. 72-81 (2000).*
Chirila, T.V. et al., Biomaterials, vol. 23, pp. 321-342 (2002).*
Peracchi, A., Rev. Med. Virol., vol. 14, pp. 47-64 (2004).*
Opalinska, J.B. et al., Nature Rev., vol. 1, pp. 503-513 (2002).*
Branch, A.D., Trends in Biochem. Sci., vol. 23, pp. 45-50 (1998).*
Crooke, S.T., Antisense Research & Application, Chapter 1, pp. 1-50 (S. Crooke, Ed. 1998) Publshed by Springer-Verlag.*
Stein et al., *Phosphorothioate Oligodeoxynucleotide Analogues*, Oligodeoxynucleotides: Antisense Inhibitors of Gene Expression, Topics in Molecular and Structural Biology (1989) vol. 12, pp. 97-117.
Ashun et al., *Inhibition of Murine Leukemia virus with Poly2'-O-(2, 4-Dinitrophenyl) Poly [A]*, Antimicrobial Agents and Chemotherapy (Oct. 1996) vol. 40, No. 10, pp. 2311-2317.
Bradbury et al., *Protein Kinase A (PK-A) Regulatory Subunit Expression in Colorectal Cancer and Related Mucosa*, Brit. J. Cancer (1994) vol. 69, pp. 738-742.
Chen et al., *Poly-2'-DNP-RNAs with Enhanced Efficacy for Inhibiting Cancer Cell Growth*, Oligonucleotides (2004) vol. 14, pp. 90-99.
Cho-Chung, *Antisense DNA Toward Type I Protein Kinase A Procedures Sustained Inhibition of Tumor Growth*, Proceedings of the Assoc. of American Physicians (1997) vol. 109, No. 1, pp. 23-32.
Kang et al., *Design of Structure-Based Reverse Transcriptase Inhibitors*, The Journal of Biological Chemistry (Apr. 2, 1994) vol. 269, No. 16, pp. 12024-12031.
Miller et al., *Types of Cyclic AMP Binding Proteins in Human Breast Cancers*, Eur. J. Cancer (1993) vol. 29A, No. 7, pp. 989-991.
Nesterova et al., *A Single-Injection Protein Kinase A-Directed Antisense Treatment to Inhibit Tumour Growth*, Nature Medicine (Jun. 1995) vol. 1, No. 6, pp. 528-533.
Nesterova et al., *Oligonucleotide Sequence-Specific Inhibition of Gene Expression, Tumor Growth Inhibition, and Modulation of cAMP Signaling by an RNA-DNA Hybrid Antisense Targeted to Protein Kinase A RI$\alpha$ Subunit*, Antisense & Nucleic Acid Drug Development (2000) vol. 10, pp. 423-433.
Rahman et al., *Selective Removal f Ribonucleases from Solution with Covalently Anchored Macromolecular Inhibitor*, Analytical chemistry (Jan. 1, 1996) vol. 68, No. 1, pp. 136-138.
Ru et al., *Specific Inhibition of Breast Cancer Cells by Antisense Poly-DNP-Oligoribonucleotides and Targeted Apoptosis*, Oncology Research (1998) vol. 10, pp: 389-397.
Ru et al., *Growth Inhibition and Antimetastic Effect of Antisense Poyl-DNP-RNA on Human Breast Cancer Cells*, Oncology Research (1999) vol. 11, pp. 505-512.
Shen et al., *A High-Efficacy Antisense RI$\alpha$ Poly-DNP 21-nt RNA*, Antisense and Nucleic Acid Drug Development (2003) vol. 13, pp. 67-74.
Summerton, *Intracellular Inactivation of Specific Nucleotide Sequences: A General Approach to the Treatment of Viral Diseases and Virally-Mediated Cancers*, J. Theor. Biol. (1979) vol. 78, pp. 77-99.

(Continued)

Primary Examiner—Jane Zara
(74) Attorney, Agent, or Firm—Hodgson Russ LLP

(57) ABSTRACT

The present invention discloses antisense poly-2'-O-(2,4-dinitrophenyl) oligoribonucleotides which are capable of down regulating the expression of the RI$_\alpha$ subunit of protein kinase A. An example is 5'-GGCUGCGUGCCUCCU-CACUGG (named antisense poly-DNP RNA-21) or a sequence which has a one-base mismatch therewith. The antisense oligoribonucleotide can be synthesized by in vitro transcription followed by chemical derivatization. The base sequence of the oligoribonucleotides is complementary to that of nt 110 to 130 in RI$_\alpha$/PKA mRNA. The antisense poly-DNP RNA-21 was found to inhibit cell growth with IC$_{50}$ values in the nanomolar range. These oligonucleotides can be used as effective anti-cancer agents.

26 Claims, 11 Drawing Sheets

OTHER PUBLICATIONS

Summerton et al., *Morpholino Antisense Oligomers: Design, Preparation, and Properties*, Antisense & Nucleic Acid Drug Development (1997) vol. 7, pp. 187-195.

Tortora et al., *The RIα Subunit of Protein Kinase A Controls Serum Dependency and Entry into Cell Cycle of Human Mammary Epithelial Cells*, Oncogene (1994) vol. 9, pp. 3233-3240.

Wang, Aihong et al., *Effective Treatment of Murine Leukemia with Antisense Poly-2'-O-(2,4-Dinitrophenyl)-Oligoribonucleotides*, Antisense & Nucleic Acid Drug Development (1999) vol. 9, pp. 43-51.

Wang, Hui et al., *Antitumor Activity and Pharmacokinetics of a Mixed-Backbone Antisense Oligonucleotide Targeted to the RIα Subunit of Protein Kinase A After Oral Administration*, Proc. Natl. Acad. Sci. (Nov. 23, 1999) vol. 96, No. 24, pp. 13989-13994.

Xin et al., *Treatment of Duck Hepatitis B. Virus by Antisense Poly-2'-O-(2,4- Dinitrophenyl)-Oligoribonucleotides*, Antisense & Nucleic Acid Drug Development (1998) vol. 8, pp. 459-468.

Zamecnik et al., *Inhibition of Rous Sarcoma Virus Replication and Cell Transformation by a Specific Oligodeoxynucleotide*, Proc. Natl. Acad. Sci. (Jan. 1978) vol. 75, No. 1, pp. 280-284.

* cited by examiner

HIGH EFFICACY ANTISENSE RIαPKA POLY-DNP OLIGORIBONUCLEOTIDES

This application claims priority to U.S. Provisional Application No. 60/431,594, filed on Dec. 5, 2002, the disclosure of which is incorporated herein by reference.

FIELD OF THE INVENTION

This invention relates generally to antisense oligonucleotides and more particularly to antisense poly-DNP oligoribonucleotides.

BACKGROUND OF THE INVENTION

Antisense oligonucleotides are oligonucleotides or analogs, whose sequence is complementary to a predetermined segment of mRNA. Typically, sequences of the antisense oligonucleotides are chosen so as to be complementary to a critical sequence in a gene so that if the gene, or mRNA transcribed therefrom, is hybridized to the complementary antisense sequence, the gene cannot be expressed or is subjected to enzymatic degradation (see U.S. Pat. No. 6,291,438, incorporated herein by reference).

The use of antisense oligonucleotides has been proposed for a variety of infections as well as proliferative disorders. In view of their sequence specificity, antisense oligonucleotides should be ideal anti-infective agents (Zamecnik and Stephenson, 1978; Summerton, 1979). However, their successful application in therapeutics has been delayed by problems of efficacy and drug delivery. Native oligonucleotides are not biomembrane-permeable. If delivered into cells with the help of amphipathic cations or liposomes, they could still be hydrolyzed by endogenous nucleases before reaching the intended targets. In order to improve bioavailability, various types of chemically modified antisense oligonucleotides have been made by solid-state synthesis and tested with different degrees of success (Summerton and Weller, 1997; Wang et al., 1999; Nesterova and Cho-Chung, 2000; Stein, 1997). In this regard, phosphorothioate oligodeoxynucleotides (PS-oligo DNA) are considered to be more resistant to nuclease digestion than corresponding phosphodiester oligodeoxynucleotides. Further, 2'-O-methyloligoribonucleotide phosphorothioates (PS-2'-O-methyloligo RNA) are considered to be more resistant to nucleases than PS-oligo DNA and can form duplexes with RNA with higher affinity. In addition, while PS-oligo RNA/RNA duplexes are not a substrate for RNase H, PS-oligo DNA/RNA duplexes are.

Solid-state synthesis of chemically modified RNA is expensive and could also lead to stereochemical complications. For example, in a solid-state synthesized 21-nt phosphorothioate, each chiral P-atom can be in $P_S$ or $P_R$ configuration so that the product is really a mixture of $2^{20}$ isomers. This stereochemical heterogeneity could give rise to non-sequence-specific toxicity.

One promising type of oligonucleotide platform is poly-2'-O-(2,4-dinitrophenyl)-oligoribonucleotide (poly-DNP-RNA) which can be synthesized by in vitro transcription with native rNTPs followed by a single step derivatization reaction. The product has no chiral P-atoms and hence is stereochemically homogeneous. It was found that poly-DNP-RNA with DNP/nucleotide molar ratio of 0.65 to 0.75 can rapidly and spontaneously cross viral envelopes (Ashun et al., 1996). It can also slowly and spontaneously cross mammalian cell membranes without transfection reagents (Ru et al., 1999). Poly-DNP-RNAs are also resistant to degradation by ribonucleases (Rahman et al., 1996; Wang, 1996).

Several antisense poly-DNP-RNAs have been synthesized and found to inhibit viral replication and cancer growth in a sequence-specific and concentration-dependent way with no non-sequence-specific toxicity in the effective concentration range (Xin and Wang, 1998; Ru et al., 1998; Ru et al., 1999). In situ hybridization experiments showed that after staying inside cancer cells for 72 h at 37° C., an antisense poly-DNP-RNA was structurally still sufficiently intact to hybridize with a biotin-labeled sense DNA probe (Ru et al., 1999). A successful in vivo application of poly-DNP-RNA has been reported in the treatment of murine leukemia. It was observed that either i.p. or oral administration of antisense poly-DNP-RNA to MMLV-infected mice eliminated not only viremia but also the DNA of the integrated viral genome in bone marrow (Wang and Wang, 1999). The observed elimination of integrated viral genome in bone marrow by oral administration of antisense poly-DNP-RNA highlighted the bioavailability of these agents. Apparently a sufficient number of the inhibitor molecules had passed through all the membrane barriers between the alimentary canal and bone marrow and reached their target in bone marrow to trigger the elimination of the infected cells, both active and resting. The infected mice that had not been treated, or those that were treated with poly-DNP-RNA of a wrong sequence all died, those that had been treated with antisense poly-DNP-RNA continued to live in apparent good health.

A common use of antisense oligonucleotides is in the field of cell proliferation disorders. An example of a gene considered to be important in cell growth regulation is the $RI_\alpha/PKA$ gene. It is considered that $RI_\alpha$ is an ontogenic growth-inducing protein, and its constitutive expression disrupts normal growth processes, resulting in proliferative disorders which can lead to malignancy. An increase in $RI_\alpha/PKA$ is an early response to the mitogenic effects of growth factors, such as GM-CSF in human leukemic cells and TGF-α in normal rat fibroblast, and phytohemagglutinin stimulation of resting lymphocytes. Increased expression of RI has also been shown to be associated with both chemical and viral carcinogenesis and oncogene-induced cell transformation. RI is the major, or sole, R subunit of PKA detected in a variety of types of human cancer cell lines and primary tumors examined (Cho-Chung, 1997). The majority of human breast cancer and colon carcinomas examined show an enhanced expression of RI and a higher ratio of PKA-I/PKA-II as compared with normal counterparts (Miller et al., 1993; Bradbury et al., 1994). Importantly, the relative overexpression of the $RI_\alpha$ subunit of PKA was associated with poor prognosis in patients with breast cancer. Conversely, downregulation of $RI_\alpha$ by site-selective cAMP analogs produces growth arrest and differentiation in a wide variety of human and rodent cancer cell lines. In addition, retroviral vector-mediated overexpression of $RI_\alpha$ provided direct evidence that $RI_\alpha$ plays a role in cell proliferation by regulating cell cycle progression (Tortora et al., 1994). These studies provide evidence that $RI_\alpha$ plays a critical role in cell proliferation. Therefore, $RI_\alpha/PKA$ is an attractive target for therapeutic approaches to malignancy.

In one study, the poly-DNP-RNA which was antisense to the $RI_\alpha$ subunit of the protein kinase A ($RI_\alpha/PKA$), was used to inhibit the growth of breast cancer cells which overexpressed this gene. The antisense poly-DNP RNA was found to be effective in a concentration dependent manner. Further, intraperitoneal administration of the antisense to SCID mice with transplanted MDA-MB-231 cells was found to inhibit the growth of the xenografts in concentration dependent manner to prevent metastasis and reduce mortality (Ru et al., 1999, Oncology Res., 11:505-512). This antisense oligonucleotide exhibited an $IC_{50}$ of about 22 nM in MCF-7 cells.

Accordingly, for the antisense oligonucleotides to be useful in the clinical setting, there continues to be a need to improve the efficacy of these compounds.

SUMMARY OF THE INVENTION

The present invention provides antisense oligoribonucleotides which have complementary nucleic acid sequences that recognize and bind the $RI_\alpha$/PKA gene or its mRNA resulting in the down-regulation of transcription or translation. The antisense oligoribonucleotides of the present invention are targeted to the sequence corresponding to nucleotides 110- 130 of the $RI_\alpha$/PKA gene.

The antisense oligoribonucleotides of the present invention can be used for down-regulating the expression of the $RI_\alpha$ subunit of the protein kinase A. In one embodiment, the antisense oligoribonucleotides can be used to inhibit the growth of cancer cells.

The antisense oligoribonucleotides of the present invention can be administered in a suitable pharmaceutical carrier to an individual to effect down-regulation of the $RI_\alpha$/PKA gene. In one embodiment, the antisense oligoribonucleotide is administered to an individual in which the $RI_\alpha$/PKA is overexpressed. Accordingly, these compositions can be used in a wide variety of conditions for inhibiting the growth of cells in which the $RI_\alpha$/PKA gene is overexpressed. In the antisense oligoribonucleotides of the present invention, one or more sugar residues are modified by the substitution of DNP at the 2'-O position.

The antisense oligoribonucleotides of the present invention can also be used for diagnostic purposes to identify the overexpression of the $RI_\alpha$/PKA gene.

In one embodiment, the sequence of the oligoribonucleotide is poly-DNP-5'-GGCUGCGUGCCUCCUCACUGG (antisense poly-DNP RNA-21 - SEQ ID NO:1). The base sequence of poly-DNP RNA-21 is complementary to that of nt 110 to 130 in $RI_\alpha$ mRNA. Also disclosed herein are permissible one-base mismatches of the SEQ ID NO:1.

Other investigators had previously synthesized a mixed backbone oligonucleotide (MBO) with the 18-nt sequence 5'-<u>GCGU</u>GCCTCCTCAC<u>UGGC</u>—wherein underlining indicates PS-2-O-methyl oligonucleotide while the rest is PS-oligo DNA (GEM 231; SEQ ID NO:2) and showed that it inhibited the growth of targeted cancer cells with an $IC_{50}$ value of 100 nM (Wang et al., 1999; Nesterova and Cho-Chung, 2000). We discovered that by adding GGCU at the 5'-end and deleting C at the 3'-end of this 18-nt sequence of GEM 231 and replacing its MBO backbone by a poly-DNP platform, the inhibition efficacy can be increased 20 to 100-fold. The observed $IC_{50}$ of antisense poly-DNP RNA-21 for the growth inhibition of MCF-7 breast cancer cells was 0.05 nM, and that for the growth inhibition of A549 lung cancer cells was about 3 nM. The control 21-nt poly-DNP-RNAs of similar structure but with scrambled, sense or multiple mismatched sequences were inactive.

BRIEF DESCRIPTION OF THE FIGURES

FIG. 7 is a representation of Western Blot analysis of $RI_\alpha$/PKA protein expression level in A549 cells. Treatments were as follows: Lane 1, untreated control; Lane 2, treated with Oligofectamine™ only; Lane 3, treated for 48 hours with 100 nM antisense poly-DNP RNA-21; Lane 4, treated for 48 hours with 100 nM 1 base mismatch ($2^{nd}$ position) poly-DNP RNA; Lane 5, treated for 48 hours with 100 nM 1 base mismatch ($19^{th}$ position) poly-DNP RNA; Lane 6, treated for 48 hours with 100 nM 1 base mismatch ($21^{st}$ position) poly-DNP RNA.

DESCRIPTION OF THE INVENTION

Figure 1A:
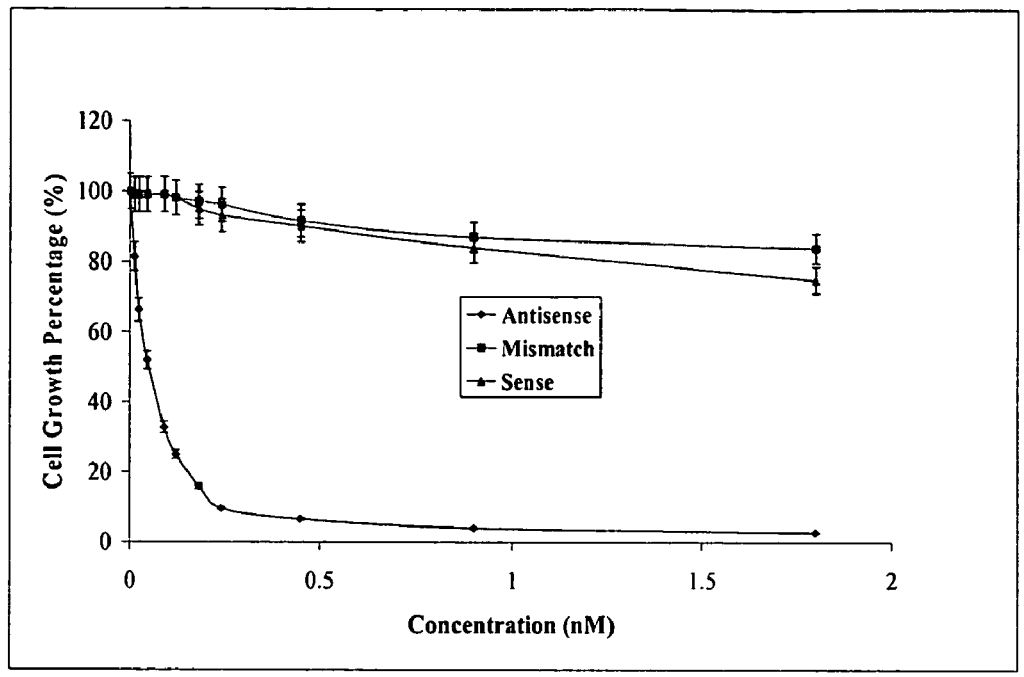
FIGS. 1A and 1B are representations of the sequence and concentration dependence of the inhibition of cell growth by antisense poly-DNP-RNAs for MCF-7 human breast cancer cells (1A) and A549 human lung adenocarcinoma cells (1B). The cells were plated at a concentration of $2 \times 10^4$ per well and then treated with different concentrations of poly-DNP-RNAs in the presence of Oligofectamine™. After 1 day of incubation, the medium was removed and replaced by fresh medium in the absence of RNA and Oligofectamine™. After incubation for 7 more days, the cells were collected and counted with a Coulter counter. Data are expressed as the percentage of growth inhibition in reference to the growth of untreated control cells. The data are presented as means±SD of four independent determinations.

The present invention provides antisense oligoribonucleotides which have complementary nucleic acid sequences that can recognize and bind to target regions of the RI$_\alpha$/PKA gene or transcribed mRNA, resulting in the down-regulation of DNA transcription, or translation of the mRNA. The antisense oligoribonucleotides provided herein inhibit the growth of cells which overexpress the RI$_\alpha$/PKA gene. In general, the antisense oligoribonucleotides are considered to bind to the mRNA and inhibit the translation thereof.

The oligoribonucleotides of the present invention include sequences which are not strictly antisense i.e., these sequences may have some bases which are not complementary to the bases in the sense strand but still have enough binding affinity for RI$_\alpha$/PKA mRNA to inhibit the growth of cells. Further, base modifications such as inosine in the oligoribonucleotides are contemplated to be within the scope of this invention.

As used herein, the letters "A" or "a" refer to adenine, "G" or "g" refer to guanine; "C" or "c" refer to cytosine; "T" or "t" refer to thymine; and "U" or "u" refer to uracil.

The oligoribonucleotides of the present invention are exemplified in the following sequence 5'-GGCUGCGUGC-CUCCUCACUGG (SEQ ID NO:1). One or more ribose residues in this sequence are modified at the 2'-O-position with a DNP group as shown below.

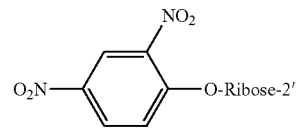

All the internuclear linkages are phosphodiester bonds.

Compared to the 20-mer antisense oligonucleotide of Ru et al., 1999 (5'-GGGCGUGCCUCCUCACUGGC—SEQ ID NO:4), in the present invention, the first two bases, GG have been replaced with GGCU and the C at the 3' end has been deleted. Further, in comparison to the 18-mer oligonucleotide of Srivastava et al., 1999 (5'-GCGTGC<u>CUCCUCACUGG</u>—SEQ ID NO:5), or to the GEM231 (<u>GCGU</u>GCCTCCTCAC<u>UGGC</u>—SEQ ID NO:2), in the present invention, four bases have been added to the 5' end, and the C at the 3' end has been deleted. Further, it should also be noted that the oligonucleotide of Srivastava et al. and GEM231 have a mixed backbone, i.e., it is made up of both deoxyribonucleotides and ribonucleotides. Thus in the sequence of Srivastava et al. and GEM231 shown above, the underlined segment indicates PS-2-O-methyl oligoribonucleotide while the rest is PS-oligo DNA.

In general, the antisense oligoribonucleotide should have a sequence which is completely complementary to the targeted portion of the RI$_\alpha$ /PKA gene. However, absolute complementarity is not required, and a sequence with one mismatch is included within the scope of this invention. It is generally known that for an oligonucleotide of about 21-25 bases, a mismatch of one base can be tolerated. Data presented herein indicates that a one-base mismatch is tolerated except when the particular mismatch is at certain positions. Thus, the antisense oligoribonucleotides of the present invention include those sequences which include a mismatch at all positions except when the mismatch is a change of U to A and G to C at positions 19 and 20 respectively. While specific permissible mismatch positions have been indicated herein, one skilled in the art may readily determine the sites of other permissible mismatches from the melting point and therefore the stability of the resulting duplex. Melting points of duplexes of a given base pair composition can be determined by standard methods (see Molecular Cloning: A Laboratory Manual (J. Sambrook et al., eds)). Combination of these with cell growth inhibition data as well as protein expression and steady state mRNA data as described herein will identify the antisense oligos with permissible mismatches.

The antisense oligoribonucleotides of the present invention include sequences of from 18-30 nucleotides comprising at least the 18 contiguous nucleotides of SEQ ID NO:20 or one-base mismatch therefrom. In a preferred embodiment, the antisense oligoribonucleotides include sequences of 21-30 nucleotides comprising at least the 21 contiguous nucleotides of SEQ ID NO:1 or one-base mismatch therefrom. In another preferred embodiment, the antisense oligoribonucleotides include sequences of from 21 to 25 nucleotides. In a more preferred embodiment, the antisense oligoribonucleotides include sequences of from 21-23 nucleotides. In a still more preferred embodiment, the antisense oligoribonucleotides are 21 nucleotides long. One or more ribos residues of the nucleotides of the present invention are modified by the substitution of DNP at the 2'-O-position. In one embodiment, about 50-80% of the ribose residues are modified DNP. In another embodiment, about 65-75% of the ribose residues are modified by DNP. The ribose residue groups that are not modified by DNP can be modified by other groups. Such modifying groups are known in the art and include 2'-O-methyl RNA(OME), 2'-O-methoxy-ethyl RNA (MOE) and 2'-fluoropyrimidine RNA. It is preferable to have some free 2'-OH groups.

The antisense oligonucleotides are most advantageously prepared by utilizing any of the known chemical oligonucleotide synthesis methods. Therefore, oligonucleotides can be made by using commercially available, automated nucleic acid synthesizers. One such device, the Applied Biosystems 380B DNA Synthesizer, utilizes β-cyanoethyl phosphoramidite chemistry. Further, many antisense oligonucleotides are commercially available. For example, Oligo Therapeutics, Inc. has a broad line of commercially available oligonucleotides and, further, provides contract manufacturing services for the preparation of oligonucleotides. In addition, custom oligonucleotides can be made by IDT, Coralville, Iowa.

The synthesis and derivatization of single stranded RNA (ssRNA) can be carried out as follows. ssRNA is synthesized through in vitro transcription as described before (Milligan et al., 1987) with slight modification. A template containing T7 promoter can be synthesized (such as custom synthesis by commercial sources). After synthesis of the RNA, it can be derivatized by reaction with a suitable reagent such as 1-fluoro-2,4,-dinitrobenzene. The derivatized RNA is purified by the standard phenol/chloroform extraction and dialysis of the aqueous layer against water. The ratio of DNP to RNA and the actual concentration of poly DNP-RNA can be calculated from the observed absorbance at 260 and 330 nm since the oligonucleotide has absorbance only at 260 nm, whereas the DNP exhibits absorbance at both wavelengths. For larger scale synthesis, the product can be separated from the reaction mixture by column adsorption and gradient elution instead of dialysis.

For administration to individuals, the antisense oligoribonucleotides of the present invention can be incorporated into convenient pharmaceutical dosage forms such as capsules, tablets, injectable, topical or inhalable preparations. Solid or liquid pharmaceutical carriers can be employed. Solid carriers include, for example, starch, calcium, sulfate dehydrate, terra alba, sucrose, talc, gelatin, agar, pectin, acacia, magnesium stearate, and stearic acid. Liquid carriers include, for example, syrup, peanut oil, olive oil, saline and water. Liposomal, viral vector, and protein conjugate preparations can also be used as carriers. Similarly, the carrier or diluent may include any prolonged release material, such as glyceryl monostearate, or glyceryl disteararate, alone or with wax. The amount of solid carrier varies widely but preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension. When a liquid carrier is used, it will most often be a saline solution or phosphate buffered solution. For intranasal delivery, aerosolized preparations can be used.

Pharmaceutical preparations can be made following conventional techniques of a pharmaceutical chemist involving mixing, granulating and compressing, when necessary, for tablet forms, or mixing, filling, and dissolving the ingredients, as appropriate, to give the desired oral or parenteral products.

Efficacious non-toxic doses of the antisense oligoribonucleotides can be determined by clinicians having ordinary skill in the art. Typically, the dose may be selected such that it results in an extracellular concentration in the vicinity of the target cells that corresponds to what has been found to be effective as shown herein. Typically, the dose may be selected from a range of 0.1 mg/kg to about 100 mg/kg, but is preferably less than 1 mg/kg. The dose can be administered to an individual, orally, rectally, by injection, or continuously. It may also be delivered to the target site, such as a tumor, directly. When administered directly to the target site, a lower dose would be required.

Even in the absence of transfection agents, poly-DNP-RNAs are slowly but spontaneously transported through mammalian cell membranes (Ashun et al., 1996; Ru et al., 1999). They are also not only resistant to hydrolysis by RNases, but may actually inhibit RNases including RNase H (Rahman et al., 1996). These last two factors may also contribute to the unusually high efficacy of poly-DNP-RNA-21 seen here.

The use of poly-DNP-RNA as a bioavailable platform for antisense RNAs has been demonstrated in the following publications: (1) Wang, A. and Wang, J. H. (1999) "Treatment of murine leukemia with poly-DNP-RNA", Antisense & Nucleic Acid Drug Development 9, 43-51; (2) Ru, K., Schmitt, S., James, W. I. and Wang, J. H. (1999) "Antitumor effect of antisense poly-DNP-RNA in vivo", Oncology Research 11, 505-572; (3) Ru, K., Taub, M. L. and Wang, J. H. (1998) "Antisense poly-DNP RNAs as specific breast cancer inhibitor", Oncology Research 10, 389-397; (4) Xin, W. and Wang, J. H. (1998), "Treatment of duck hepatitis B by poly-DNP-RNA", Antisense & Nucleic Drug Development 8, 459-468.

Various types of chemically modified antisense oligonucleotides targeted at the often overexpressed $RI_\alpha$ gene have been successfully applied to inhibit cancer cell growth (Cho-Chung et al., 1997; Nesterova and Cho-Chung, 1995; 2000; Srivastava et al., 1999; Wang et al., 1999; Ru et al., 1998; Ru et al., 1999). The most successful example is a mixed backbone oligonucleotide (MBO) with the 18-base sequence 5'-GCGUGCCTCCTCACUGGC (GEM231—SEQ ID NO:2) (Wang et al., 1999). GEM231 has an $IC_{50}$ value of 5-10 μM in MCF-7 cells and 100 nM in A549 cells. Thus for inhibiting cancer cell growth, the present poly-DNP-RNA-21 is several orders of magnitude more potent than GEM 231.

Previous studies already showed that treatment of cancer cells with chemically modified antisense oligonucleotide can trigger apoptosis in a sequence-specific way (Srivastava et al., 1998; Ru et al., 1998). The present work confirms that the antisense poly-DNP-RNA-21 can kill the targeted cancer cells by silencing the $RI_\alpha$ gene, activating caspase-8 and inducing apoptosis.

The present oligoribonucleotide can be administered to an individual including humans in which the $RI_\alpha$/PKA gene is overexpressed. As discussed in the background section, this gene has been reported to be overexpressed in proliferative disorders such as cancer. In the use of the oligonucletides of this invention, both single stranded as well as double stranded oligoribonucleotides can be used. The oligoribonucleotides may be administered so as to effect a reduction in the growth of cells which overexpress the $RI_\alpha$/PKA gene. The regimen may comprise one or more doses given within a short period of time or over an extended period of time. The present antisense oligoribonucleotide may be administered alone or in combination with other therapeutic approaches such as surgical intervention, radiation, immunotherapy or chemotherapy.

Since the poly-DNP-RNA-21 of the present invention can be used to arrest or inhibit the growth of cells which overexpress the $RI_\alpha$/PKA gene, it could be used as an anti-cancer agent with the following advantages over other chemically modified oligoribonucleotides made by solid-state synthesis:

1. The synthesis of poly-DNP-RNA-21 by in vitro transcription followed by one-step derivatization reaction is simpler and the product has no stereochemical impurities.
2. DNP-RNAs are delivered faster into mammalian cells and remain active for days inside the cells.
3. Since only extremely low dosage of poly-DNP-RNA-21 is required, sequence-independent non-specific toxicity should be negligible.

The antisense oligoribonucleotides of the present invention and/or complementary sequences thereof, can also be used for diagnostic purposes such as to detect the overexpression of the $RI_\alpha$/PKA gene. For example, nucleic acids (mRNA or reverse transcribed DNA) can be isolated from test and control samples and hybridization reactions carried out with the oligoribonucleotides provided herein. Hybridization of nucleic acid sequences are well known to those in the art and are used routinely. Thus, conditions for hybridization can be easily determined. Any increase in hybridization in the test sample over the control sample is indicative of overexpression of the $RI_\alpha$/PKA.

This invention is further described in the examples provided below which are intended to be illustrative and are not intended to be restrictive in any way.

EXAMPLE 1

This embodiment describes the preparation and derivatization of the antisense RNA. The templates with $T_7$ Promoter for in vitro transcription were customer synthesized by IDT (Integrated DNA Technologies, Coralville, Iowa). The DNA templates used for synthesizing the antisense strand of $RI_\alpha$ oligo RNA were 5'-CTCAGCTGTAATACGACTCACTAT-AGGCTGCGTGCCTCCTCACTGG-3' (SEQ ID NO:6) and 5'-CCAGTGAGGAGGCACGCAGCCTATAGT-GAGTCGTATTACAGCTGAG-3' (SEQ ID NO:7). The method of in vitro transcription was described previously (Milligan et al., 1987). Briefly, the reaction was run in 50 mM Tris Buffer (pH 8.1), 5 mM dithiothreitol, 1 mM spermidine, 0.2 µg/µl BSA, 25 mM $MgCl_2$, 5 mM NTPs, 30 µg/ml DNA template, 0.2 U/µl RNasing Ribonuclease inhibitor (Promega, Madison, Wis.), 2 U/ml pyrophosphates (Sigma), 2 U/el $T_7$ RNA polymerase (Promega). The reaction mixtures were incubated at 37° C. for 8 h. Then 30 units RQ1 RNase-free DNase (Promega) were added to the reaction mixtures and incubated at 37° C. for additional 30 minutes. After digestion, the reaction mixtures were extracted with phenol and chloroform and precipitated with ethanol. The yield of the RNA product was determined by measuring optical density at 260 nm.

The RNA was derivatized as described previously (Kang and Wang, 1994) with some modification. RNA (4 mg) was dissolved in 1800 µl of water and mixed with 450 µl of buffer solution (2 M $KHCO_3$, 0.1 M $K_2CO_3$, pH 8.8). Then 1 ml of acetone containing 160 µl of 1-fluoro-2,4-dinitrobenzene (Sigma) was added to the reaction mixtures. The reaction was incubated at 45° C. for 5-6 hour, and the pH value was maintained around 8.8. After that, the reaction was extracted with phenol/chloroform. The resulting mixture was dialyzed against water for 3 days to remove excess 1-fluoro-2,4-dinitrobenzene. The ratio of DNP/RNA (0.7) and the actual concentration of poly-DNP-RNA were calculated from the observed absorbance at 260 and 330 nm.

EXAMPLE 2

This embodiment describes the sequence-specific inhibition of cancer cell growth by antisense poly-DNP-RNA-21. To illustrate this embodiment, experiments were performed on two human cancer cell lines purchased from ATCC (Rockville, Md.). MCF-7 human breast cancer cells were grown in Minimum Essential Medium (MEM) α Medium supplemented with 10% fetal bovine serum (FBS) (GIBCO-BRL, Grand Island, N.Y.) and Insulin (5 mg/ml) (Sigma, St. Louis, Mo.). A549 human lung adenocarcinoma cells were grown in F-12 Nutrient Mixture (Ham) supplemented with 10% FBS (GIBCO-BRL). Cells were grown in a humidified atmosphere of 95% air and 5% $CO_2$ at 37° C.

To increase the delivery of antisense poly-DNP-RNA into cells in culture, Oligofectamine™ reagent (GIBCO-BRL) was used in the poly-DNP-RNA treatment. About $2 \times 10^4$ cells were plated on 12 well plates 1 day before the treatment. Then $RI_\alpha$/PKA antisense or control poly-DNP-RNAs were added at various concentrations in the presence of Oligofectamine™ (1 µl/ml). Both types of cells were incubated for 8 days with antisense poly-DNP-RNA-21, sense poly-DNP-RNA, and 5-base mismatched poly-DNP-RNA. Cells were then counted with a Coulter counter and double-checked with Trypan Blue staining. All samples were run in quadruplicate. Cells treated with Oligofectamine™ alone exhibited no cytotoxicity under any experimental conditions.

Figure 1B:
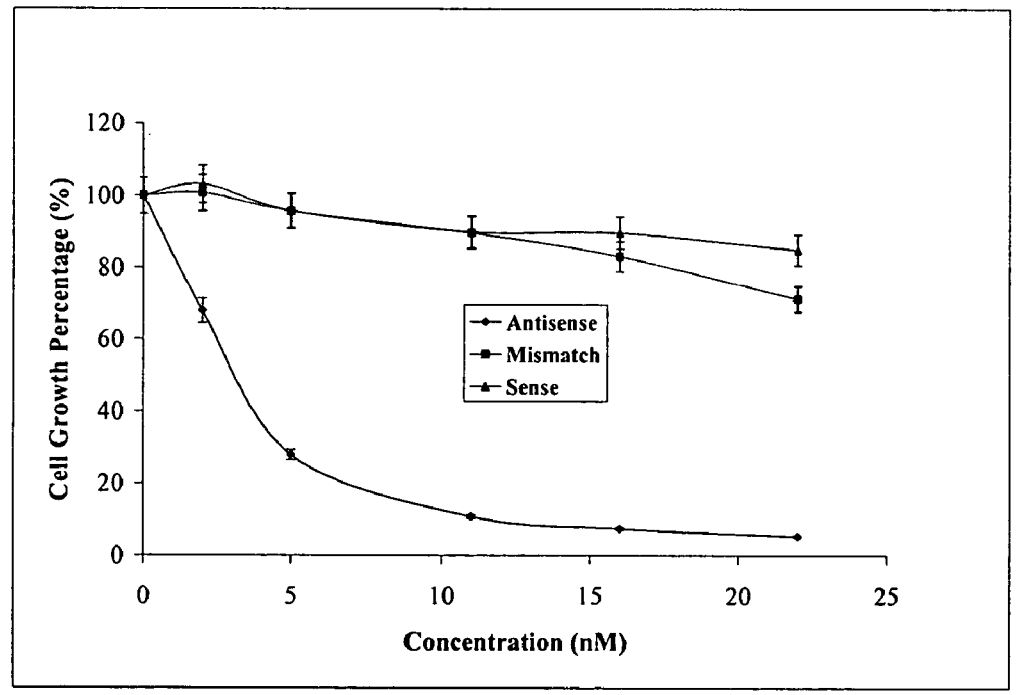

FIG. 1 shows the concentration-dependent and sequence-specific inhibition of the growth of MCF-7 cells and that of A549 cells respectively by the antisense inhibitor poly-DNP-RNA-21. The base-sequences of the three 21-nt poly-DNP-RNA in FIG. 1 are:

```
Antisense    5'-GGCUGCGUGCCUCCUCACUGG  (SEQ ID NO:1)

Sense        5'-GGCCAGUGAGGAGGCACGCAG  (SEQ ID NO:8)

Mismatched   5'-GGGUGCCUGCAUCCACACAGG  (SEQ ID NO:9)
``` where each underlined base represents a mismatch. Compared to the antisense poly-DNP-RNA-21, the sense and 5-base mismatched control Poly-DNP-21 nt RNAs are essentially inactive. The $IC_{50}$ values of poly-DNP-RNA-21 observed in MCF-7 cells and in A549 cells were 0.05 nM and 3 nM respectively which compare favorably with the corresponding $IC_{50}$ values of GEM 231 (5,000-10,000 nM in MCF-7 cells and 100 nM in A549 cells —Wang et al., 1999).

EXAMPLE 3

In this example, studies were carried out in parallel to compare the efficacy of the oligoribonucleotide of the present invention with GEM231 under identical conditions. In addition, an oligonucleotide (MBO-21) which is the same sequence as the antisense oligoribonucleotide of SEQ ID NO:1, but with the mixed backbone of GEM231 was also used. Accordingly, the sequence of the MBO-21 oligonucleotide is as follows—5' GGCUGCGTGCCTCCTCACUGG (SEQ ID NO:3) wherein the underlined segment was PS-2-O-methyl oligoribonucleotide while the rest is PS-oligo DNA.

The effect of these three oligonucleotides was determined on MCF-7 cells and A549 cells under identical conditions. The results are presented in Table 1.

TABLE 1

IC$_{50}$ values of oligonucleotide derivatives
as specific inhibitors of growth of targeted cells.

| Oligo | IC$_{50}$ | |
|---|---|---|
| | MCF-7 | A549 |
| poly-DNP-RNA-21 (21-mer) | 0.05 nM | 3 nM |
| GEM231 (18-mer) | 45 nM | 100 nM |
| MBO-21 (21-mer) | 30 nM | 80 nM |

These results confirm the comparative results in Example 2. The data shows that poly-DNP-RNA-21 (SEQ ID NO:1) is 25-fold more efficient than GEM231 in A549 cells and 900-fold more efficient than GEM231 in MCF-7 cells. The poly-DNP-RNA-21 is also more efficient than MBO-21 which has the same sequence as the poly-DNP-RNA-21 but has a different backbone. Thus, it appears that both the sequence and the backbone contribute to the increased efficacy of the oligoribonucleotides of the present invention.

EXAMPLE 4

The preceding experiments (FIG. 1) demonstrated that RI$_\alpha$ antisense poly-DNP-RNA can inhibit the growth of cancer cells in a sequence-specific manner. Since it is generally assumed that antisense inhibitors achieve cell growth inhibition through suppressing the expression of specific target genes, the effect of antisense poly-DNP-RNA-21 on the steady-state concentrations of its complementary mRNA was examined by RT-PCR assay. The specific mRNAs for β-actin and RI$_\alpha$/PKA were amplified by their respective primers, and the relative concentrations of the corresponding cDNAs were estimated by comparing the intensities of ethidium-stained bands in the same electrophoresis gel. The experiments were carried out as follows.

MCF-7 cells (2×10$^5$/well) were plated in 6-well plates one day before being treated with 10 nM poly-DNP-RNAs in the presence of Oligofectamine™. After incubation with poly-DNP-RNAs for 24 h, the cells were lysed and total RNAs were extracted using Absolutely RNA™ RT-PCR Miniprep Kit (Stratagene, La Jolla, Calif.).

The subsequent reverse transcription was carried out in the presence 2 μl Oligo (dT)$_{12-18}$ (500 μg/ml) primer, reaction buffer, 0.5 mM dNTP Mix, 10 mM DTT (GIBCO-BRL), 2 U/μl RNasin® Ribonuclease inhibitor(Promega), and 20 U/μl M-MLV reverse transcriptase (GIBCO-BRL). The reaction was run at 39° C. for 1 h followed by incubation at 90° C. for 10 min. About ½0 of the mixture containing the cDNA from the reverse transcription reaction was amplified with PCR in a final volume of 25 μl. The PCR reaction was performed as described with some modification. The 21 cycles of the PCR (1 min at 94° C., 1 min at 60° C., and 1 min 30 sec at 72° C.) were preceded by 4 min of denaturation at 94° C. and followed by 5 min of elongation at 72° C. The PCR reaction mixture has a composition of 1×reaction buffer (20 mM Tris-HCL (pH 8.4), 50 mM KCl, 200 μM each of dNTPs, 1.5 mM MgCl$_2$, 0.2 μM each of the primers and 2.5 U Platinum® Taq DNA polymerase (GIBCO-BRL).

Figure 2:
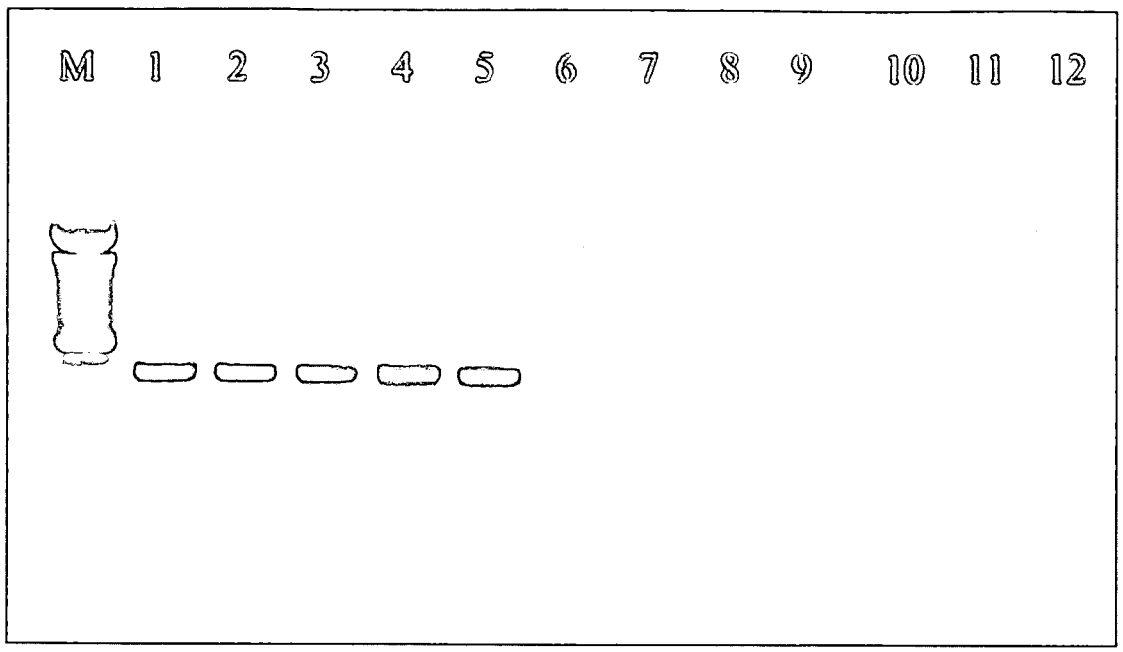
FIG. 2 is a representation of the effect of antisense poly-DNP-RNAs on the steady-state concentration of mRNAs determined by RT-PCR assay. The amplified cDNA bands are shown in twelve lanes on the right of the molecular weight ladder in 1.5% agarose gel. Lanes 1-6 are amplified with actin primers. Lanes 7-12 are amplified with $RI_\alpha$/PKA primers. Lanes 1 and 7, cells without any treatment. Lanes 2 and 8, cells treated with Oligofectamine™ only. Lanes 3 and 9, cells treated with antisense poly-DNP-RNA-21. Lanes 4 and 10, cells treated with a 5-base mismatched poly-DNP-RNA. Lanes 5 and 11, cells treated with sense poly-DNP-RNA. Lanes 6 and 12, negative control without adding cDNA to the PCR mixture.

As shown in FIG. 2, treatments of MCF-7 cells with antisense poly-DNP-RNA-21 did not change the mRNA level of β-actin, which was used as the internal standard, but decreased the steady-state concentration of RI$_\alpha$ mRNA to an undetectable level. In contrast, sense or 5-base mismatched poly-DNP-RNA had no significant effect on the steady-state concentration of RI$_\alpha$ mRNA.

EXAMPLE 5

The sequence-specific antisense inhibition of cell growth was further confirmed by measuring the effect of the antisense poly-DNP-RNA-21 on the expression of the target gene products (RI$_\alpha$ protein) by Western blotting analysis. Cell extracts were prepared as follows. Cells (2×10$^5$/well) were plated in 6-well plates one day before treatment with 10 nM poly-DNP-RNAs in the presence of Oligofectamine™. After incubation of MCF-7 cells with poly-DNP-RNAs for 24 h, cells were washed once with PBS and lysed with 200 μl boiling lysis buffer (1% SDS, 1.0 mM sodium ortho-vanadate, 10 mM Tris pH 7.4). Protein concentration was determined by BCA Protein Assay Reagent Kit (Pierce, Rockford, Ill.), using bovine serum albumin (BSA) as a standard.

Following preparation of cell extracts, total protein (20 μg) was run on NuPAGE® 4-12% Bis-Tris Gel with MOPS running buffer and then transferred to Invitrolon™ PVDF membranes (Invitrogen, Carlsbad, Calif.). Blotted membranes were developed using WesternBreeze® Novex Chromogenic Western Blot Immunodetection Kit (Invitrogen). Monoclonal antibodies against RI$_\alpha$, Bid, Bcl-2, and Caspase-8 were purchased from BD Biosciences (San Diego, Calif.).

Figure 3:
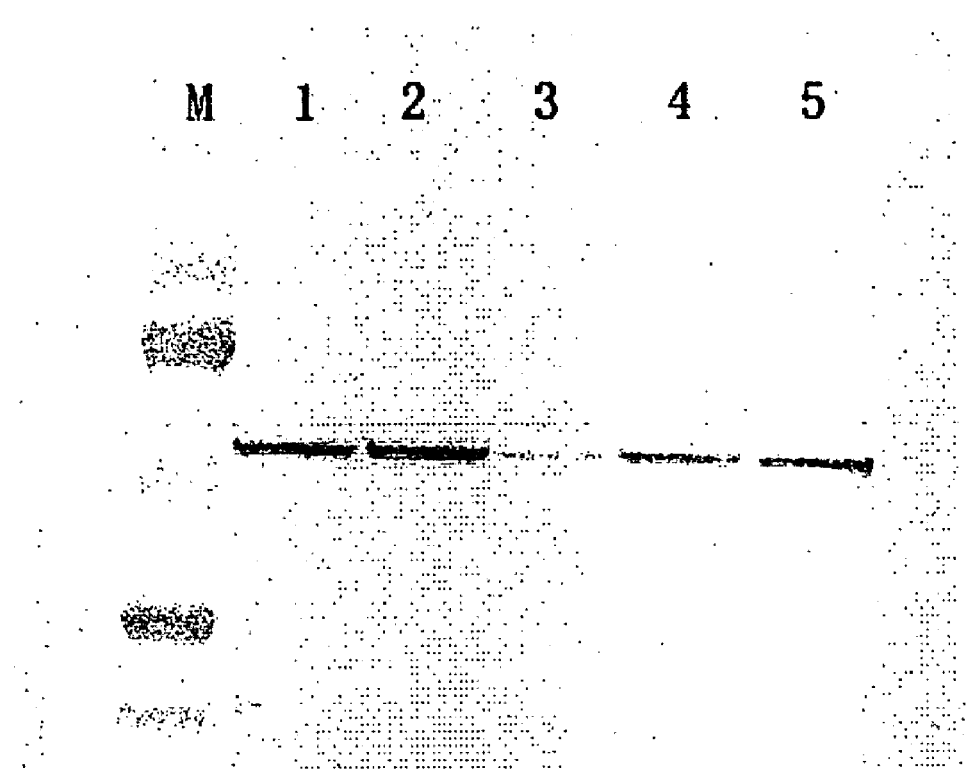
FIG. 3 is a representation of Western blot analysis of PKA $RI_\alpha$ protein expression level. Treatments were as follows: Lane 1, untreated control; Lane 2, treated with Oligofectamine™ only; Lane 3, treated with antisense poly-DNP-RNA-21; Lane 4, treated with 5-base mismatched poly-DNP-RNA; Lane 5, treated with sense poly-DNP-RNA.

FIG. 3 illustrates the effect on RI, protein expression of different poly-DNP-RNAs at same concentration. In antisense poly-DNP-RNA-21 treated MCF-7 cells, the expression level of RI$_\alpha$ protein was barely detectable, whereas in the sense and 5-base mismatched poly-DNP-RNA treated cells, the expression levels of RI$_\alpha$ protein were comparable to those in the untreated control cells.

EXAMPLE 6

A previous study showed that inhibition of growth of cancer cells by antisense poly-DNP-RNAs results in apoptosis (Ru et al., 1998). This example describes the effect of an antisense oligoribonucleotide of the present invention on the status of proteins related to the apoptosis pathway. The molecular events involved in the activation of apoptosis signal transduction pathway was studied by Western blotting analysis. Cells were treated with poly-DNP RNAs and processed for Western blotting as described in Example 5.

Figure 4:
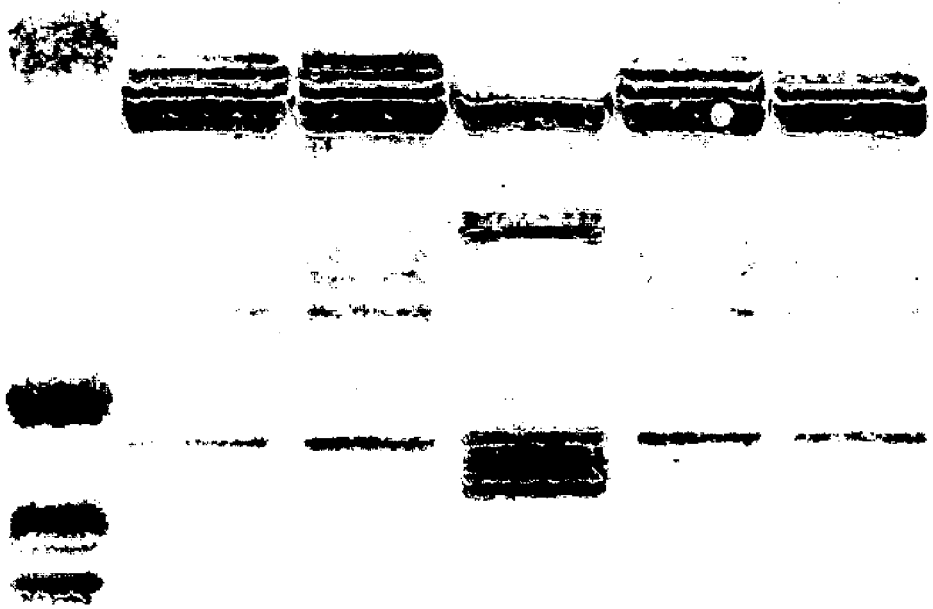
FIG. 4 is a representation of Western blot analysis of sequence-specific activation of Caspase-8. Treatments were as follows: Lane 1, untreated control; Lane 2, treated with Oligofectamine™ only; Lane 3, treated with antisense poly-DNP-RNA-21; Lane 4, treated with 5-base mismatched poly-DNP-RNA; Lane 5, treated with sense poly-DNP-RNA.
Figure 5:
FIG. 5 is a representation of Western blot analysis of sequence-specific cleavage of Bid. Treatments were as follows: Lane 1, untreated control; Lane 2, treated with Oligofectamine™ only control; Lane 3, treated with antisense poly-DNP-RNA-21; Lane 4, treated with 5-base mismatched poly-DNP-RNA; Lane 5, treated with sense poly-DNP-RNA.

As shown in FIG. 4, when MCF-7 cells had been treated with antisense poly-DNP-RNA for 24 h, activation of caspase-8 was indicated by the disappearance of the procaspase band and the formation of two smaller activated subunits of caspase-8. The activation of caspase-8 was sequence-specific because when MCF-7 cells were treated with either sense or 5-base mismatched poly-DNP-RNA, the procaspase-8 still remained intact after 24 h incubation. In addition, as shown in FIG. 5, Bid also depleted in a sequence specific manner.

Among the numerous factors known to modulate the apoptosis signal transduction pathway, caspase-8 is the key initiator caspase in the death-receptor pathway (Hengartner, 2000). Caspase-8 is produced as a proenzyme (55/50 kDa doublet) which upon receptor aggregation is proteolytically cleaved into smaller subunits of 40/36 (doublet), and 23 kDa (Boesen-de Cock et al., 1998; 1999). Cross-talk and integration between the death receptor and mitochondrial pathways is provided by Bid, a pro-apoptotic Bcl-2 family member. Caspase-8 mediated cleavage of Bid greatly increases its pro-death activity, and results in its translocation to mitochondria, where it promotes cytochrome c exit (Hengartner, 2000). The observed effects on Bid are consistent with its role in apoptosis.

EXAMPLE 7

Figure 6:
FIG. 6 is a representation of Western blot analysis of sequence-specific cleavage of Bcl-2. Treatments were as follows: Lane 1, untreated control; Lane 2, treated with Oligofectamine™ only; Lane 3, treated with antisense poly-DNP-RNA-21; Lane 4, treated with 5-base mismatched poly-DNP-RNA; Lane 5, treated with sense poly-DNP-RNA.

This example describes the effect of treatment with an antisense oligoribonucleotide of the present invention on the status of Bcl-2 protein. High expression of Bcl-2 has been shown in human breast cancer cell lines (Haldar et al., 1994). As an anti-apoptotic factor, Bcl-2 protein blocks apoptotic stimuli such as growth factor deprivation, radiation, heat-shock, virus and most of the chemotherapeutic agents (Hockenbery et al., 1990; Reed, 1995). As shown in FIG. 6, in MCF-7 cells treated with antisense poly-DNP-RNA-21, the expression level of Bcl-2 protein had been reduced significantly compared to those treated with sense and 5-base mismatched poly-DNP-RNA.

EXAMPLE 8

This embodiment demonstrates that a one-base mismatch is permissible for the antisense oligoribonucleotides of the present invention. For this example, the bases in SEQ ID NO:1 were replaced at indicated positions as shown in the Table 3 and $IC_{50}$ was determined for A549 cells. As shown in Table 2, the antisense oligoribonucleotide without any replacements has an $IC_{50}$ of about 3 nM. When single replacements were made at positions up to 18 and then at position 21, the oligoribonucleotide was still effective at comparable concentrations. However, when a change was made at positions 19 and 20, as indicated in Table 2, the oligoribonucleotides were found to be inactive.

TABLE 2

Positional Dependence of the Effect of Single Mismatch on the Inhibition of AS-RI$_\alpha$ Poly-DNP-RNA in A549 Cells

| Position of Mismatch | Mutation | SEQ ID NO: | IC50 (nM) | Inhibition Efficacy |
|---|---|---|---|---|
| none | none | 1 | 3.0 | + |
| 21 | G→C | 10 | 12 | + |
| 20 | G→C | 11 | inactive | − |
| 19 | U→A | 12 | inactive | − |
| 18 | C→G | 13 | 20 | + |
| 17 | A→U | 14 | 9 | + |
| 16 | C→G | 15 | 8 | + |
| 15 | U→A | 16 | 7.5 | + |
| 14 | C→A | 17 | 5.6 | + |
| 11 | C→A | 18 | 4.5 | + |
| 2 | G→C | 19 | 3.5 | + |

Figure 7:
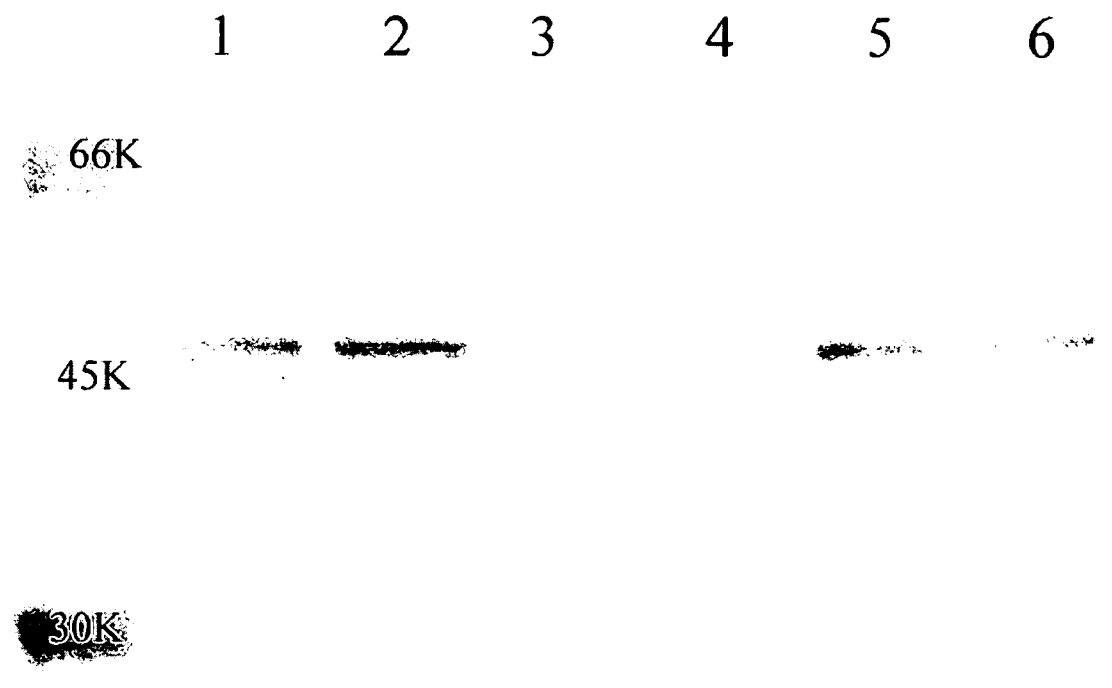

To confirm that changes of U to A and G to C at positions 19 and 20 respectively, were not permissible while mismatches at other positions were permissible, Western blot analysis of the RI$_\alpha$/PKA protein was carried out in A549 cells incubated with mismatches at positions 2, 19 and 21. The results are shown in FIG. 7. These results indicate that untreated controls expressed RI$_\alpha$/PKA (Lane 1) and treatment with the transfecting agent only, did not decrease this expression (Lane 2). However, when these cells were treated with the antisense poly-DNP-RNA-21 (SEQ ID NO:1), a significant decrease in the expression of RI$_\alpha$/PKA was observed (Lane 3). A reduction was also observed for the mismatch at position 2 (Lane 4) and position 21 (Lane 6). However, no reduction was observed when the mismatch was at position 19 (Lane 5).

Figure 8:
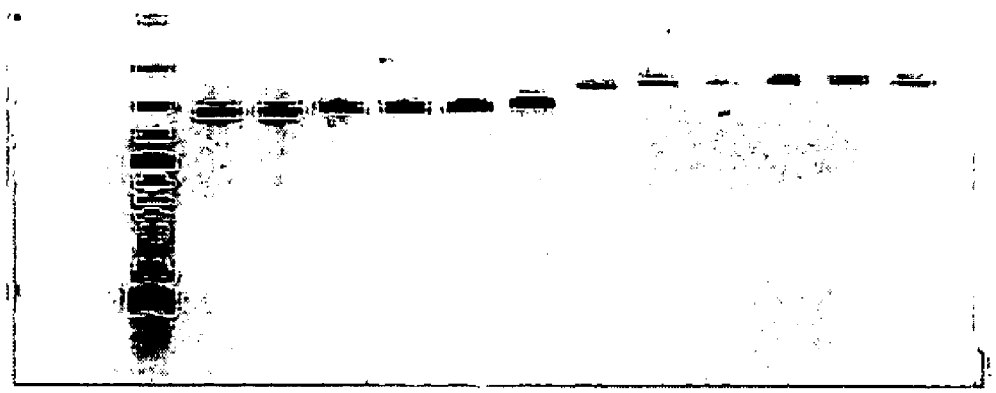
FIG. 8 is a representation of the effect of 48 hour treatment with 100 nM poly-DNP-RNA on the steady-state concentration of mRNA in A549 cells, determined by RT-PCR assay. The amplified cDNA bands are shown in 12 lanes to the right of the molecular weight ladder (M) in 1.5% agarose gel. Lanes 1-6, amplified with actin primers; Lanes 7-12, amplified with $RI_\alpha$/PKA primers; Lanes 1 and 7, cells without any treatment; Lanes 2 and 8, cells treated with Oligofectamine™; Lanes 3 and 9, cells treated with antisense poly-DNP-RNA-21; Lanes 4 and 10, cells treated with 1-base mismatch poly-DNP-RNA ($2^{nd}$ position); Lanes 5 and 11, cells treated with 1-base mismatch poly-DNP-RNA ($19^{th}$ position); Lanes 6 and 11, cells treated with 1-base mismatch poly-DNP-RNA ($21^{st}$ position).

In another experiment, the effect of some of the one-base mismatches was determined on the steady-state levels of mRNA for RI$_\alpha$/PKA. A549 cells were incubated with one-base mismatches at positions 2, 19 and 21 and RT-PCR was carried out. Primers used for actin were 5'-GGGATAGCA-CAGCCTGGATAGCA-3' (SEQ ID NO:24) and 5'-GAT-GATATCGCCGCGCTCGTCGTC-3'(SEQ ID NO:25) and primers used for RI$_\alpha$/PKA were 5'-GCTAAAGCGGCCAT-TGTCTTGT-3' (SEQ ID NO:26) and 5'-AGTACCGCCGC-CAGTGAGGAGG-3' (SEQ ID NO:27). The results are shown in FIG. 8. The results indicate that control cells showed RI$_\alpha$/PKA (Lane 7) which was not affected by the transfecting agent alone (Lane 8). However, the poly-DNP RNA of SEQ ID NO:1, reduced the concentration of the RI$_\alpha$/PKA mRNA (Lane 9). A similar effect was observed for the one-base mismatch at position 2 (Lane 10). The one-base mismatch at position 21 also appears to reduce the level (Lane 12). However, the one-base mismatch at position 19 (Lane 11) did not reduce the level as compared to controls. This experiment further confirms that one-base mismatches are permissible except when U at position 19 is changed to A and G at position 20 is changed to C. Based on the data and description provided herein other permissible mismatches at various positions can be determined by those skilled in the art.

EXAMPLE 9

Figure 9:
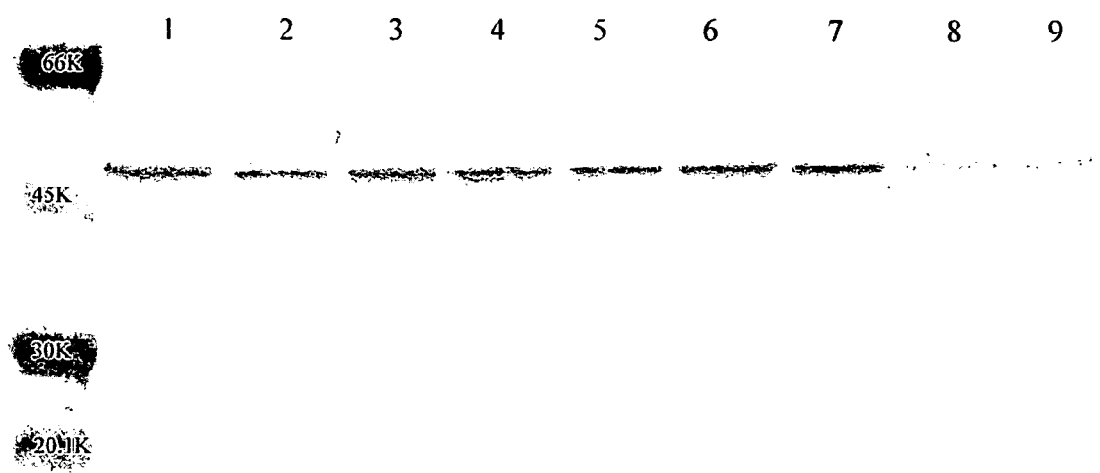
FIG. 9 is a representation of Western Blot analysis of RI$_\alpha$/PKA protein expression level in MCF-7 cells. Treatments were as follows: Lane 1, treated with 300 nM MBO-21 for 48 hours; Lane 2, treated with 600 nM MBO-21 for 48 hours; Lane 3, treated with 1200 nM MBO-21 for 48 hours; Lane 4, treated with 300 nM GEM231 for 48 hours; Lane 5, treated with 600 nM GEM231 for 48 hours; Lane 6, treated with 1200 nM GEM231 for 48 hours; Lane 7, treated with 20 nM poly-DNP-RNA-21 for 48 hours; Lane 8, treated with 50 nM poly-DNP-RNA-21 for 48 hours; Lane 9, treated with 100 nM poly-DNP-RNA-21 for 48 hours.

In this embodiment, the efficacy of the antisense poly-DNP-RNA-21 of the present invention was compared to the mixed backbone sequence of MBO-21 (SEQ ID NO:3) and to GEM231 (SEQ ID NO:2) with respect to the effect on the expression of RI$_\alpha$/PKA. To carry out this experiment, MCF-7 cells were incubated with the antisense poly-DNP RNA-21, MBO-21 and GEM231. After various times, the expression of RI$_\alpha$/PKA was evaluated by Western blotting. The results are shown in FIG. 9. The results show that no significant reduction in the expression of RI$_\alpha$/PKA was observed with MBO-21 and GEM231 even up to concentrations of 1.2 µM while a significant effect was observed with 50 and 100 nM for the poly DNP oligonucleotide of the present invention. These data indicate that gene silencing efficacy of the poly-DNP-RNA-21 is several folds higher than either the MBO-21 or the GEM231.

EXAMPLE 10

This embodiment describes the growth inhibiting ability of antisense oligoribonucleotides of varying lengths. For this experiment, antisense oligoribonucleotides of 18, 20, 21 and 23 bases were synthesized and derivatized with DNP as described in Example 1. The sequence of the 21-mer used in this experiment is the same as SEQ ID NO:1. For the 18-mer, the three 3' end nucleotides, UGG, were deleted and for the 20-mer, the last 3' end nucleotide G was deleted. For the 23 mer, two nucleotides, CG were added to the 3' end to provide the sequence poly-DNP-5'-GGCUGCGUGCCUCCU-CACUGGCG (SEQ ID NO:22). Cell growth assays were carried out as described in Example 2 on A549 and MCF-7 cells. The results are shown in Table 3 below.

TABLE 3

Values for cell growth inhibition by RI$_\alpha$/PKA targeting antisense DNP-RNA of different lengths.

| Length | Sequence | SEQ ID NO: | MCF-7 |
|---|---|---|---|
| 18 | 5'-GGCUGCGUGCCUCCUCAC | 20 | ~20-30 nM |
| 20 | 5'-GGCUGCGUGCCUCCUCACUG | 21 | ~20-30 nM |

TABLE 3-continued

Values for cell growth inhibition by RI$_\alpha$/PKA targeting antisense DNP-RNA of different lengths.

| Length | Sequence | SEQ ID NO: | MCF-7 |
|---|---|---|---|
| 21 | 5'-GGCUGCGUGCCUCCUCACUGG | 1 | 0.05 nM |
| 23 | 5'-GGCUGCGUGCCUCCUCACUGGCG | 22 | 0.8 nM |

These results indicate that truncating the 3' end of SEQ ID NO:1 results in an oligoribonucleotide which is active but not to the same extent as poly-DNP-RNA-21. However, extending the 3' end results in an antisense oligoribonucleotide which is comparable to the poly-DNP-RNA-21 for inhibiting the growth of cells.

EXAMPLE 11

This example describes the thermal denaturation of duplex oligonucleotides. The thermal denaturation of duplex oligonucleotides was monitored by UV-absorption at 260 nm. For comparison the denaturation curves of four duplex oligonucleotides with different backbones but identical sequence of bases, except for the replacement of U by T in DNA are shown in FIG. 10.

Figure 10:
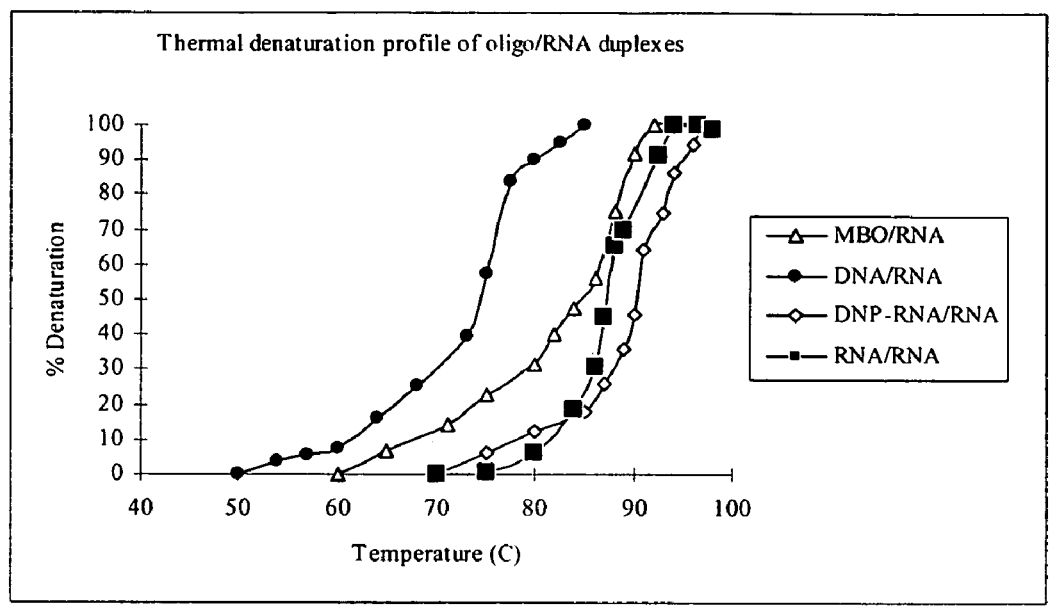
FIG. 10 is a representation of the thermal denaturation of duplex oligonucleotides with different backbones but identical sequences except for the replacement of U by T in DNA. Thus, in the RNA/RNA duplex, the strands have the sequence of 5'-poly-DNP-GGCUGCGUGCCUCCUCACUGG (SEQ ID NO:1) and its complement; in the DNA/RNA duplex, the strands have the sequence of SEQ ID NO:1 (DNA, wherein the U's are replaced by T's) and its complementary RNA strand; in the DNP-RNA/RNA, one strand has the sequence of SEQ ID NO:1, wherein the ribose residues are modified with DNP as described in Example 1; and in MBO/RNA, the structure of the antisense strand with mixed backbone is 5-GGCUGCGTGCCTCCTCACUGG (referred to herein as MBO-21—SEQ ID NO:3), wherein the underlined nucleosides are O-methylribonucleotides and the remaining are deoxyribonucleosides, and all internuclear linkages are phosphorothioate.

Among the four duplexes examined in FIG. 10, poly-DNP-RNA/RNA has the highest hybridization affinity. The observation that the transition temperature of poly-DNP-RNA/RNA is even higher than that of native RNA/RNA (siRNA) indicates that the DNP-groups not only do not interfere with base-pairing but may aid hybridization via weaker interactions. These observations also suggest that during the derivatization of RNA by the present procedure, the bases themselves are not modified with DNP.

EXAMPLE 12

This embodiment describes the use of the antisense oligoribonucleotides of the present invention to arrest or reduce the growth of malignant cells. The antisense oligoribonucleotides can be administered to an individual who has been diagnosed with cancer in which the cells overexpress this gene. A detailed description of various methods that are known in the art for therapeutic applications of antisense oligoribonucleotides have been provided.

For this embodiment, human cancer xenograft models can be established by standard methods (see Wang et al., 1999). Briefly, SCID mice can be commercially obtained. Cells (such as A549 and MDA-MB231) can be cultured and harvested in a suitable medium (such as Ham's F-12 optionally containing basement membrane matrix), and injected or implanted into the mice. The cells can be monitored by general clinical observation, determination of body weight and tumor weight. Tumor growth can be recorded and tumor mass calculated from the two perpendicular diameters of the implant. For determination of the effect of poly-DNP RNAs, the oligoribonucleotides are dissolved in a suitable carrier such as physiological saline and administered (such as i.p.). The volume, dose and frequency of oligos injected can be varied. Control animals can be administered the sense oligoribonucleotide or scrambled sequence oligoribonucleotide. Tumor growth of the xenografts, and other parameters such as expression of RI$_\alpha$/PKA can be studied in the mice and compared to controls.

Figure 11:
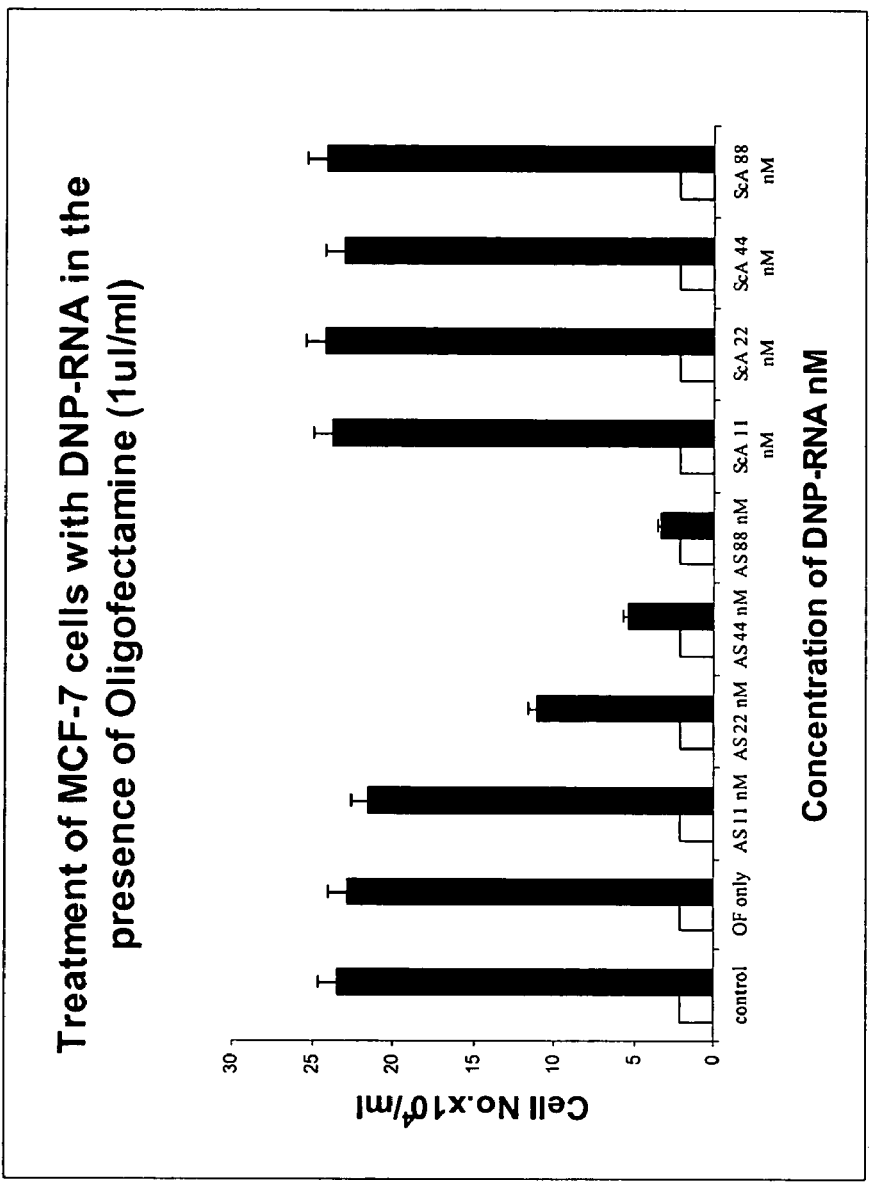
FIG. 11 is a representation of the growth inhibitory effects of an antisense oligonucleotide of Ru et al. (1999) which has a sequence of poly-DNP-5'-GGGCGUGCCUCCU-CACUGGC (SEQ ID NO:4). Open bars represent cells at day 0 and closed bars represent cell growth at day 7. Data are shown for control, Oligofectamine™ only, Oligofectamine™ with: SEQ ID NO:4 at indicated concentrations and a scrambled sequence SCA 5'-GGGAGUCGCUCCGUC-CUCGC 3' (SEQ ID NO:23) at indicated concentrations.

In this regard, it is also important to note that an antisense oligonucleotide of 20 nucleotides in length (SEQ ID NO:4), which has 17 nucleotides common with the present nucleotide, was shown to be effective in vivo in SCID mice in which MDA-MB-231 cells had been implanted (Ru et al., 1999). The present antisense oligoribonucleotide is of a comparable length and nucleotides 5-21 of the present antisense oligoribonucleotide poly-DNP-RNA-21 are identical to the 20-mer of Ru et al. oligonucleotide. To compare the efficacy of the antisense oligonucleotide of Ru et al., MCF-7 cells were treated with poly-DNP-RNA of SEQ ID NO:4 and a scrambled sequence 5'-GGGAGUCGCUCCGUCCUCGC 3' (SEQ ID NO:23). The results are shown in FIG. 11. The IC$_{50}$ for the antisense oligonucleotide of SEQ ID NO:4 is about 22 nM. These results show that the present antisense oligonucleotide is several folds more efficacious than SEQ ID NO:4. Since SEQ ID NO:4 has been demonstrated to have in vivo effects, the present antisense oligoribonucleotide is expected to be more efficacious than SEQ ID NO:4 in vivo also.

Another oligonucleotide, GEM231, a mixed backbone oligo targeting the RI$_\alpha$/PKA gene has been shown to be effective in vivo and is currently undergoing clinical trials (Wang et al., 1999). As demonstrated herein the antisense oligonucleotide of the present invention is more efficacious than either the 20 mer of Ru et al. or the 18-mer mixed backbone GEM231. Thus, it is expected that similar administration of the antisense oligoribonucleotide of the present invention in vivo will provide for an efficacious arrest or inhibition of growth of cancer cells.

While specific embodiments have been presented herein, routine modifications will be apparent to those skilled in the art and are intended to be within the scope of the invention.

REFERENCES

Ashun, M. A., Hu, Y., Kang, I., Li, C. C., and Wang, J. H. (1996): Inhibition of murine leukemia virus with poly-2'-O-(2,4-dinitrophenyl)poly[A]. Antimicrob. Agents Chemother. 40, 2311-7.

Boesen-De Cock, J. G., Tepper, A. D., De Vries, E., Van Blitterswijk, W. J., and Borst, J. (1998): CD95 (Fas/APO-1) induces ceramide formation and apoptosis in the absence of a functional acid sphingomyelinase. J. Biol. Chem. 273, 7560-5.

Boesen-De Cock, J. G., Tepper, A. D., De Vries, E., Van Blitterswijk, W. J., and Borst, J. (1999): Common regulation of apoptosis signaling induced by CD95 and the DNA-damaging stimuli etoposide and gamma-radiation downstream from caspase-8 activation. J. Biol. Chem. 274, 14255-61.

Bradbury, A. W., Carter, D. C., Miller, W. R., Cho-Chung, Y. S. and CLair, T (1994): Protein kinase A (PK-A) regulating subunit expression in colorectal cancer and related mucosa. Brit. J. Cancer, 69:738-742.

Cho-Chung, Y. S., Nesterova, M., Kondrashin, A., Noguchi, K., Srivastava, R., and Pepe, S. (1997): Antisense-protein kinase A: a single-gene-based therapeutic approach. Antisense Nucleic Acid Drug Dev. 7, 217-23.

Cho-Chung (1997): Antisense DNA toward type I protein kinase A produces sustained inhibition of tumor growth. Proc. Assoc. Amer. Physic., 109:23-32.

Haldar, S., Negrini, M., Monne, M., Sabbioni, S., and Croce, C. M. (1994): Down-regulation of bcl-2 by p53 in breast cancer cells. Cancer Res. 54, 2095-7.

Hengartner, M. O. (2000): The biochemistry of apoptosis. [see comments.]. Nature 407, 770-6.

Hockenberry, D., Nunez, G., Milliman, C., Schreiber, R. D., and Korsmeyer, S. J. (1990): Bcl-2 is an inner mitochondrial membrane protein that blocks programmed cell death. Nature 348, 334-6.

Kang, I., and Wang, J. H. (1994): Design of structure-based reverse transcriptase inhibitors. J. Biol. Chem. 269, 12024-31.

Miller, W. R., Hulme, M. J., Cho-Chung, Y. S. and Elton, R. A. (1993): Types of cyclic AMP binding proteins-in human breast cancers. Eur. J. Cancer, 29A, 989-991.

Milligan, J. F.; Goebe, D. R.; Witherell, G. W.; Uhlenbeck, O. C. (1987): Oligoribonucleotide synthesis using T7 RNA polymerase and synthetic DNA templates. Nucleic Acids Research 15: 8783-8798.

Nesterova, M., and Cho-Chung, Y. S. (1995): A single-injection protein kinase A-directed antisense treatment to inhibit tumour growth. Nat. Med. 1, 528-33.

Nesterova, M., and Cho-Chung, Y. S. (2000): Oligonucleotide sequence-specific inhibition of gene expression, tumor growth inhibition, and modulation of cAMP signaling by an RNA-DNA hybrid antisense targeted to protein kinase A RIalpha subunit. Antisense Nucleic Acid Drug Dev. 10, 423-33.

Rahman, M. H., Kang, I., Waterbury, R. G., Narang, U., Bright, F. V., and Wang, J. H. (1996): Selective removal of ribonucleases from solution with covalently anchored macromolecular inhibitor. Analytical Chem. 68, 134-8.

Reed, J. C. (1995): Regulation of apoptosis by bcl-2 family proteins and its role in cancer and chemoresistance. Curr. Opin. Oncol. 7, 541-6.

Ru, K., Schmitt, S., James, W. I., and Wang, J. H. (1999): Growth inhibition and antimetastatic effect of antisense poly-DNP-RNA on human breast cancer cells. Oncol. Res. 11, 505-12.

Ru, K., Taub, M. L., and Wang, J. H. (1998): Specific inhibition of breast cancer cells by antisense poly-DNP-oligoribonucleotides and targeted apoptosis. Oncol. Res. 10, 389-97.

Srivastava, R. K., Srivastava, A. R., Park, Y. G., Agrawal, S., and Cho-Chung, Y. S. (1998): Antisense depletion of RIalpha subunit of protein kinase A induces apoptosis and growth arrest in human breast cancer cells. Breast Cancer Res. Treat. 49, 97-107.

Srivastava, R. K., Srivastava, A. R., Seth, P., Agrawal, S., and Cho-Chung, Y. S. (1999): Growth arrest and induction of apoptosis in breast cancer cells by antisense depletion of protein kinase A-RI alpha subunit: p53-independent mechanism of action. Mol. Cell. Biochem. 195, 25-36.

Stein, C. C., J. (1997): Oligodeoxyribonucleotides: Antisense Inhibitors of Gene Expression. CRC Press Inc. Boca Raton, Fla.pp.Pages.

Summerton, J. (1979): Intracellular inactivation of specific nucleotide sequences: a general approach to the treatment of viral diseases and virally-mediated cancers. J. Theor. Biol. 78, 77-99.

Summerton, J., and Weller, D. (1997): Morpholino antisense oligomers: design, preparation, and properties. Antisense Nucleic Acid Drug Dev. 7, 187-95.

Tortora, G., Pepe, S., Bianco, C., Baldassarre, G., Budillon, A., Clair, T., Cho-Chung, Y. S., Bianco, A. R. and Ciardiello, F. (1994): The RI alpha subunit of protein kinase A controls serum dependency and entry into cell cycle of human mammary epithelial cells. Oncogene, 9:3233-3240.

Wang, A., and Wang, J. H. (1999): Effective treatment of murine leukemia with antisense poly-2'O-(2,4-dinitrophenyl)-oligoribonucleotides. Antisense Nucleic Acid Drug Dev. 9, 43-51.

Wang, H., Cai, Q., Zeng, X., Yu, D., Agrawal, S., and Zhang, R. (1999): Antitumor activity and pharmacokinetics of a mixed-backbone antisense oligonucleotide targeted to the RIalpha subunit of protein kinase A after oral administration. Proc. Natl. Acad. Sci. U.S.A. 96, 13989-94.

Wang, J. H. K., I.;Rahman, M. H. (1996): Composition and Methods of Application of reactive Antiviral Polyadenylic Acid derivatives.: U.S. Pat. No. 5,496,546.

Xin, W., and Wang, J. H. (1998): Treatment of duck hepatitis B virus by antisense poly-2'-O-(2,4-dinitrophenyl)-oligoribonucleotides. Antisense Nucleic Acid Drug Dev. 8, 459-68.

Zamecnik, P. C., and Stephenson, M. L. (1978): Inhibition of Rous sarcoma virus replication and cell transformation by a specific oligodeoxynucleotide. Proc. Natl. Acad. Sci. U.S.A. 75, 280-4.

---

We claim:

1. An oligoribonucleotide consisting of from 21 to 23 nucleotides comprising:
   the contiguous sequence of SEQ ID NO:1 or a sequence which has one-base mismatch with SEQ ID NO:1,
   wherein the ribose residue of at least one nucleotide is protected at the 2'-O- position by 2, 4-dinitrophenyl (DNP) and wherein the oligoribonucleotide is capable of down-regulating the expression of the $RI_\alpha$ subunit of protein kinase A.

2. The oligoribonucleotide of claim 1, wherein the oligoribonucleotide consists of a sequence selected from the group consisting of SEQ ID NO:1, SEQ ID NO:10, SEQ ID NO:13, SEQ ID NO:14, SEQ ID NO:15, SEQ ID NO:16, SEQ ID NO:17, SEQ ID NO:18, SEQ ID NO:19 and SEQ ID NO:22.

3. The oligoribonucleotide of claim 2, wherein the oligoribonucleotide is SEQ ID NO:1.

4. The oligoribonucleotide of claim 1, wherein the one-base mismatch consists of a sequence selected from the group consisting of SEQ ID NO:10, SEQ ID NO:13, SEQ ID NO:14, SEQ ID NO:15, SEQ ID NO:16, SEQ ID NO:17, SEQ ID NO:18 and SEQ ID NO:19.

5. The oligoribonucleotide of claim 1, wherein the DNP to nucleotide molar ratio is between 0.5 to 0.8.

6. The oligoribonucleotide of claim 5, wherein the DNP to nucleotide molar ratio is between 0.65 to 0.75.

7. A composition comprising the oligoribonucleotide of claim 1.

8. The composition of claim 7, further a comprising a complementary strand to the oligoribonucleotide.

9. The composition of claim 7 further comprising a pharmaceutically acceptable carrier.

10. The composition of claim 9, further comprising a chemotherapeutic agent.

11. The composition of claim 7, wherein the oligoribonucleotide has a sequence selected from the group consisting of SEQ ID NO:1, SEQ ID NO:10, SEQ ID NO:13, SEQ ID NO:14, SEQ ID NO:15, SEQ ID NO:16, SEQ ID NO:17, SEQ ID NO:18, SEQ ID NO:19, SEQ ID NO:22 and combinations thereof.

12. The composition of claim 11, wherein the oligoribonucleotide consists of the sequence of SEQ ID NO:1.

13. A method of down regulating the expression of $RI_\alpha$/PKA gene in a cell comprising providing to the cell the oligoribonucleotide of claim 1 in an amount effective to down-regulate the expression of the $RI_\alpha$/PKA gene.

14. The method of claim 13, wherein the sequence of the oligoribonucleotide consists of a sequence selected from the group consisting of SEQ ID NO:1, SEQ ID NO:10, SEQ ID NO:13, SEQ ID NO:14, SEQ ID NO:15, SEQ ID NO:16, SEQ ID NO:17, SEQ ID NO:18, SEQ ID NO:19, SEQ ID NO:22 and combinations thereof.

15. The method of claim 14, wherein the sequence of the oligoribonucleotide is SEQ ID NO:1.

16. A method of reducing the growth of cells which over-express the $RI_\alpha$/PKA gene comprising providing to the cells a composition comprising the oligoribonucleotide of claim 1 in an amount effective to reduce the growth of the cells.

17. The method of claim 16, wherein the sequence of the oligoribonucleotide consists of a sequence selected from the group consisting of SEQ ID NO:1, SEQ ID NO:10, SEQ ID NO:13, SEQ ID NO:14, SEQ ID NO:15, SEQ ID NO:16, SEQ ID NO:17, SEQ ID NO:18, SEQ ID NO:19 and SEQ ID NO:22.

18. The method of claim 17, wherein the sequence of the oligoribonucleotide is SEQ ID NO:1.

19. A method of reducing the growth of cancer cells in an individual comprising administering to the individual a growth inhibiting regimen of the composition of claim 7.

20. The method of claim 19, wherein the sequence of the oligoribonucleotide in the composition consists of a sequence selected from the group consisting of SEQ ID NO:1, SEQ ID NO:10, SEQ ID NO:13, SEQ ID NO:14, SEQ ID NO:15, SEQ ID NO:16, SEQ ID NO:17, SEQ ID NO:18, SEQ ID NO:19, SEQ ID NO:22 and combinations thereof.

21. The method of claim 20, wherein the sequence of the oligoribonucleotide is SEQ ID NO:1.

22. The method of claim 19, wherein the administration of the composition is combined with a treatment selected from the group consisting of surgery, radiation, chemotherapy and immunotherapy.

23. The method of claim 19, wherein the composition is administered via a route selected from the group consisting of intratumoral, intravenous, intraperitoneal, intramuscular, intranasal, oral, topical and rectal.

24. An oligoribonucleotide consisting of 18 nucleotides comprising:
   the contiguous sequence of SEQ ID NO:20 or a sequence which has one-base mismatch with SEQ ID NO:20,
   wherein the ribose residue of at least one nucleotide is protected at the 2'-O- position by 2, 4-dinitrophenyl (DNP) and wherein the oligoribonucleotide is capable of down-regulating the expression of the $RI_\alpha$ subunit of protein kinase A.

25. The oligoribonucleotide of claim 24, which consists of the sequence of SEQ ID NO:20.

26. A composition comprising the oligoribonucleotide of claim 24.

* * * * *

SEQUENCE LISTING

```
<160> NUMBER OF SEQ ID NOS: 27

<210> SEQ ID NO 1
<211> LENGTH: 21
<212> TYPE: RNA
<213> ORGANISM: artificial sequence
<220> FEATURE:
<223> OTHER INFORMATION: Antisense oligoribunucleotide poly-DNP-RNA-21

<400> SEQUENCE: 1
ggcugcgugc cuccucacug g                                               21

<210> SEQ ID NO 2
<211> LENGTH: 18
<212> TYPE: DNA
<213> ORGANISM: artificial sequence
<220> FEATURE:
<223> OTHER INFORMATION: Mixed backbone (DNA/RNA)oligonucleotide -
      GEM231
```

```
<400> SEQUENCE: 2
gcgugcctcc tcacuggc                                                      18

<210> SEQ ID NO 3
<211> LENGTH: 21
<212> TYPE: DNA
<213> ORGANISM: artificial sequence
<220> FEATURE:
<223> OTHER INFORMATION: Mixed backbone (DNA/RNA)oligonucleotide -
                        MBO-21

<400> SEQUENCE: 3
ggcugcgtgc ctcctcacug g                                                  21

<210> SEQ ID NO 4
<211> LENGTH: 20
<212> TYPE: RNA
<213> ORGANISM: artificial sequence
<220> FEATURE:
<223> OTHER INFORMATION: Antisense oligonucleotide of Ru et al., 1999

<400> SEQUENCE: 4
gggcgugccu ccucacuggc                                                    20

<210> SEQ ID NO 5
<211> LENGTH: 18
<212> TYPE: DNA
<213> ORGANISM: artificial sequence
<220> FEATURE:
<223> OTHER INFORMATION: Mixed backbone (DNA/RNA) Oligonucleotide of
                        Srivasta et al., 1999

<400> SEQUENCE: 5
gcgtgcctcc ucactggc                                                      18

<210> SEQ ID NO 6
<211> LENGTH: 46
<212> TYPE: DNA
<213> ORGANISM: artificial sequence
<220> FEATURE:
<223> OTHER INFORMATION: DNA template for synthesis of antisense strand
                        of RI-alpha

<400> SEQUENCE: 6
ctcagctgta atacgactca ctataggctg cgtgcctcct cactgg                       46

<210> SEQ ID NO 7
<211> LENGTH: 46
<212> TYPE: DNA
<213> ORGANISM: artificial sequence
<220> FEATURE:
<223> OTHER INFORMATION: DNA template for synthesis of antisense strand
                        of RI-alpha

<400> SEQUENCE: 7
ccagtgagga ggcacgcagc ctatagtgag tcgtattaca gctgag                       46

<210> SEQ ID NO 8
<211> LENGTH: 21
<212> TYPE: DNA
<213> ORGANISM: artificial sequence
<220> FEATURE:
<223> OTHER INFORMATION: Sense strand

<400> SEQUENCE: 8
ggccagugag gaggcacgca g                                                  21
```

<210> SEQ ID NO 9
<211> LENGTH: 21
<212> TYPE: DNA
<213> ORGANISM: artificial sequence
<220> FEATURE:
<223> OTHER INFORMATION: 5-base mismatched strand

<400> SEQUENCE: 9
gggugccugc auccacacag g                                              21

<210> SEQ ID NO 10
<211> LENGTH: 21
<212> TYPE: RNA
<213> ORGANISM: artificial sequence
<220> FEATURE:
<223> OTHER INFORMATION: One-base mismatch at position 21 with poly-
      DNP-RNA-21

<400> SEQUENCE: 10
ggcugcgugc cuccucacug c                                              21

<210> SEQ ID NO 11
<211> LENGTH: 21
<212> TYPE: RNA
<213> ORGANISM: artificial sequence
<220> FEATURE:
<223> OTHER INFORMATION: One-base mismatch at position 20 with poly-
      DNP-RNA-21

<400> SEQUENCE: 11
ggcugcgugc cuccucacuc g                                              21

<210> SEQ ID NO 12
<211> LENGTH: 21
<212> TYPE: RNA
<213> ORGANISM: artificial sequence
<220> FEATURE:
<223> OTHER INFORMATION: One-base mismatch at position 19 of poly-DNP-
      RNA-21

<400> SEQUENCE: 12
ggcugcgugc cuccucacag g                                              21

<210> SEQ ID NO 13
<211> LENGTH: 21
<212> TYPE: RNA
<213> ORGANISM: artificial sequence
<220> FEATURE:
<223> OTHER INFORMATION: One-base mismatch at position 18 of poly-DNP-
      RNA-21

<400> SEQUENCE: 13
ggcugcgugc cuccucagug g                                              21

<210> SEQ ID NO 14
<211> LENGTH: 21
<212> TYPE: RNA
<213> ORGANISM: artificial sequence
<220> FEATURE:
<223> OTHER INFORMATION: One-base mismatch at position 17 of poly-DNP-
      RNA-21

<400> SEQUENCE: 14
ggcugcgugc cuccucucug g                                              21

```
<210> SEQ ID NO 15
<211> LENGTH: 21
<212> TYPE: RNA
<213> ORGANISM: artificial sequence
<220> FEATURE:
<223> OTHER INFORMATION: One-base mismatch at position 16 of poly-DNP-
      RNA-21

<400> SEQUENCE: 15
ggcugcgugc cuccugacug g                                              21

<210> SEQ ID NO 16
<211> LENGTH: 21
<212> TYPE: RNA
<213> ORGANISM: artificial sequence
<220> FEATURE:
<223> OTHER INFORMATION: One-base mismatch at position 15 of poly-DNP-
      RNA-21

<400> SEQUENCE: 16
ggcugcgugc cuccacacug g                                              21

<210> SEQ ID NO 17
<211> LENGTH: 21
<212> TYPE: RNA
<213> ORGANISM: artificial sequence
<220> FEATURE:
<223> OTHER INFORMATION: One-base mismatch at position 14 of poly-DNP-
      RNA-21

<400> SEQUENCE: 17
ggcugcgugc cucaucacug g                                              21

<210> SEQ ID NO 18
<211> LENGTH: 21
<212> TYPE: RNA
<213> ORGANISM: artificial sequence
<220> FEATURE:
<223> OTHER INFORMATION: One-base mismatch at position 11 of poly-DNP-
      RNA-21

<400> SEQUENCE: 18
ggcugcgugc auccucacug g                                              21

<210> SEQ ID NO 19
<211> LENGTH: 21
<212> TYPE: RNA
<213> ORGANISM: artificial sequence
<220> FEATURE:
<223> OTHER INFORMATION: One-base mismatch at position 2 of poly-DNP-
      RNA-21

<400> SEQUENCE: 19
gccugcgugc cuccucacug g                                              21

<210> SEQ ID NO 20
<211> LENGTH: 18
<212> TYPE: RNA
<213> ORGANISM: artificial sequence
<220> FEATURE:
<223> OTHER INFORMATION: Antisense oligoribunucleotide 18-mer

<400> SEQUENCE: 20
ggcugcgugc cuccucac                                                  18
```

```
<210> SEQ ID NO 21
<211> LENGTH: 20
<212> TYPE: RNA
<213> ORGANISM: artificial sequence
<220> FEATURE:
<223> OTHER INFORMATION: Antisense oligoribunucleotide 20-mer

<400> SEQUENCE: 21
ggcugcgugc cuccucacug                                              20

<210> SEQ ID NO 22
<211> LENGTH: 23
<212> TYPE: RNA
<213> ORGANISM: artificial sequence
<220> FEATURE:
<223> OTHER INFORMATION: Antisense oligoribunucleotide 22-mer

<400> SEQUENCE: 22
ggcugcgugc cuccucacug gcg                                          23

<210> SEQ ID NO 23
<211> LENGTH: 20
<212> TYPE: RNA
<213> ORGANISM: artificial sequence
<220> FEATURE:
<223> OTHER INFORMATION: Scrambled sequence control

<400> SEQUENCE: 23
gggagucgcu ccguccucgc                                              20

<210> SEQ ID NO 24
<211> LENGTH: 23
<212> TYPE: DNA
<213> ORGANISM: artificial sequence
<220> FEATURE:
<223> OTHER INFORMATION: PCR down primer for actin

<400> SEQUENCE: 24
gggatagcac agcctggata gca                                          23

<210> SEQ ID NO 25
<211> LENGTH: 24
<212> TYPE: DNA
<213> ORGANISM: artificial sequence
<220> FEATURE:
<223> OTHER INFORMATION: PCR up primer for Actin

<400> SEQUENCE: 25
gatgatatcg ccgcgctcgt cgtc                                         24

<210> SEQ ID NO 26
<211> LENGTH: 22
<212> TYPE: DNA
<213> ORGANISM: artificial sequence
<220> FEATURE:
<223> OTHER INFORMATION: PCR down primer for RI alpha PKA

<400> SEQUENCE: 26
gctaaagcgg ccattgtctt gt                                           22

<210> SEQ ID NO 27
<211> LENGTH: 22
<212> TYPE: DNA
<213> ORGANISM: artificial sequence
<220> FEATURE:
<223> OTHER INFORMATION: PCR up primer for RI alpha PKA
```

```
<400> SEQUENCE: 27
agtaccgccg ccagtgagga gg                                                    22
```